US00PP37630P3

(12) United States Plant Patent
Williams

(10) Patent No.: US PP37,630 P3
(45) Date of Patent: Aug. 18, 2026

(54) ***COLOCASIA* PLANT NAMED 'COMASTA'**

(50) Latin Name: ***Colocasia esculenta* (L.) Schott.**
Varietal Denomination: COMASTA

(71) Applicant: Brian's Botanicals, Louisville, KY (US)

(72) Inventor: Brian Paul Williams, Louisville, KY (US)

( * ) Notice: Subject to any disclaimer, the term of this patent is extended or adjusted under 35 U.S.C. 154(b) by 0 days.

(21) Appl. No.: 18/831,475

(22) Filed: Feb. 6, 2025

(65) Prior Publication Data

US 2026/0231842 P1 Aug. 6, 2026

(51) Int. Cl.
*A01H 5/12* (2018.01)
*A01H 6/10* (2018.01)

(52) U.S. Cl.
USPC ..... Plt./373
CPC ..... *A01H 6/10* (2018.05); *A01H 5/12* (2013.01)

(58) Field of Classification Search
USPC ..... Plt./373, 258
CPC ..... A01H 5/12; A01H 5/00; A01H 6/10
See application file for complete search history.

(56) References Cited

U.S. PATENT DOCUMENTS

PP36,569 P2 * 3/2025 Williams ..... Plt./373

OTHER PUBLICATIONS

Bandus *Colocasia* x 'Madeira Star' 2025 retrieved on Nov. 5, 2025 at https://www.bandus.nl/koop/colocasia-x-madeira-star-olifantsoor/, 4 pp. (Year: 2025).*

* cited by examiner

*Primary Examiner* — June Hwu
(74) *Attorney, Agent, or Firm* — Samuel R. McCoy, Jr.

(57) ABSTRACT

'COMASTA' is a distinctive *Colocasia* plant which is characterized by an upright and clumping growth habit with broadly cordate and strongly rugose foliage borne on relatively long purple petioles, green juvenile foliage with a unique yellow-white star-like pattern in the central portion of the lamina, and violet to dark green mature foliage with a vibrant red-purple star-like pattern in the central portion of the lamina. These characteristics have been found true to type and stable throughout generations.

3 Drawing Sheets

Latin name of the genus and species: The Latin name of the genus and species of the novel variety disclosed herein is *Colocasia esculenta* (L.) Schott.

Variety denomination: The inventive variety of *Colocasia* disclosed herein has been given the variety denomination 'COMASTA'.

BACKGROUND OF THE INVENTION

Parentage: 'COMASTA' originated as a seedling selection, resulting from the controlled pollination of the proprietary seed parent, a *Colocasia esculenta* 'ColMad1' (not patented), and the proprietary pollen parent, *Colocasia esculenta* 'ColMad2' (not patented). Both parents were developed and owned by the inventor and were never commercially released. The cross was performed by the inventor at a commercial greenhouse in Louisville, Kentucky, United States in September of 2013. Seeds from said cross were harvested, then germinated; the resulting seedlings were grown to a mature size in order to further evaluate desirable commercial characteristics. In September of 2018, the inventor selected the claimed *Colocasia* plant for commercialization due to its unique foliage coloration and foliar variegation pattern.

Asexual Reproduction: Asexual reproduction of 'COMASTA' by way of rooting cormels harvested from the corm, and later by way of meristematic tissue culture propagation, was first performed in April of 2014 at a commercial greenhouse in Louisville, Kentucky. Through four subsequent generations, the plants so produced have shown that the unique features of the instant cultivar are stable and reproduced true to type.

SUMMARY OF THE INVENTION

The cultivar 'COMASTA' has not been observed under all possible environmental conditions and the phenotype may vary somewhat with variations in the instant environment such as temperature, day length, and light intensity, without, however, any variance in genotype. The following characteristics have been repeatedly observed and represent the distinguishing characteristics of the new *Colocasia* cultivar 'COMASTA'. These traits, in combination, distinguish 'COMASTA' as a new and distinct cultivar.

1. *Colocasia* 'COMASTA' exhibits an upright, basally-clumping growth habit with broad cordate foliage borne on relatively long petioles that arise directly from the base of the plant; and
2. *Colocasia* 'COMASTA' exhibits strongly rugose foliage with repand margins; and
3. *Colocasia* 'COMASTA' exhibits petioles that are yellow-green transitioning to dark purple as the plant matures; and
4. *Colocasia* 'COMASTA' exhibits green juvenile foliage with a yellow-white coloration adjacent to the main vein and proximal portions of the lateral veins, appearing as a unique star-like pattern in the central portion of the lamina; and 5. *Colocasia* 'COMASTA' exhibits violet to dark green mature foliage with a vibrant red-purple coloration adjacent to the main vein and proximal portions of the lateral veins, appearing as a unique star-like pattern in the central portion of the lamina.

BOTANICAL DESCRIPTION OF THE PLANT

Figure 1:
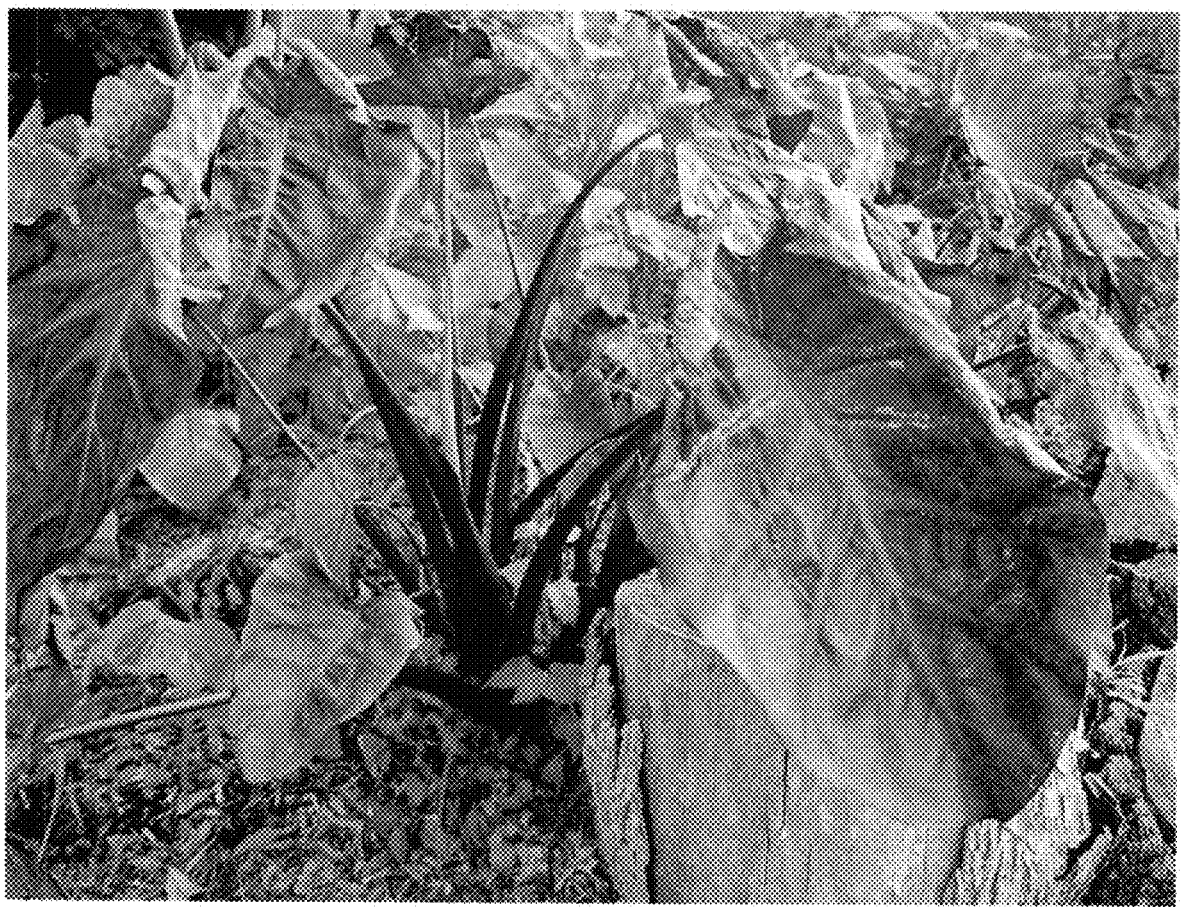
FIG. 1 illustrates, as nearly true as it is reasonably possible to make the same in color photographs of this type, an exemplary mature 'COMASTA' plant. This plant was grown in its entirety outside in full sun at a nursery in Louisville, Kentucky, United States and is approximately 12 months old.
Figure 2:
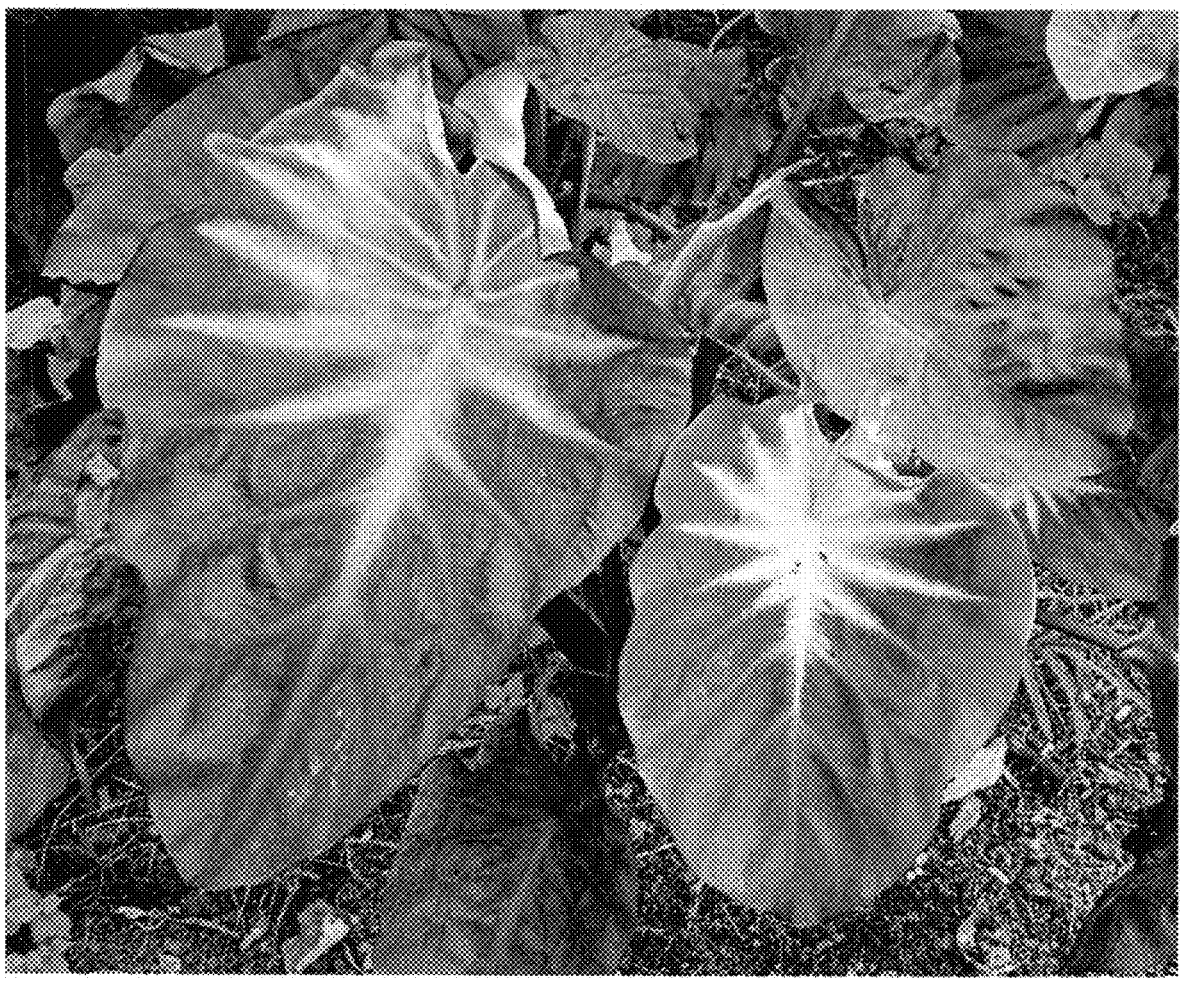
FIG. 2 illustrates, as nearly true as it is reasonably possible to make the same in color photographs of this type, an exemplary 'COMASTA' plant in an intermediary life stage, displaying a nearly-mature lamina at the 9 o'clock position, mature laminas at the 2 and 6 o'clock positions and a lamina in the transitional stage at the 3 o'clock position. The plant show is approximately 9 months old. This plant was grown in its entirety outside in full sun at a nursery in Louisville, Kentucky, United States.
Figure 3:
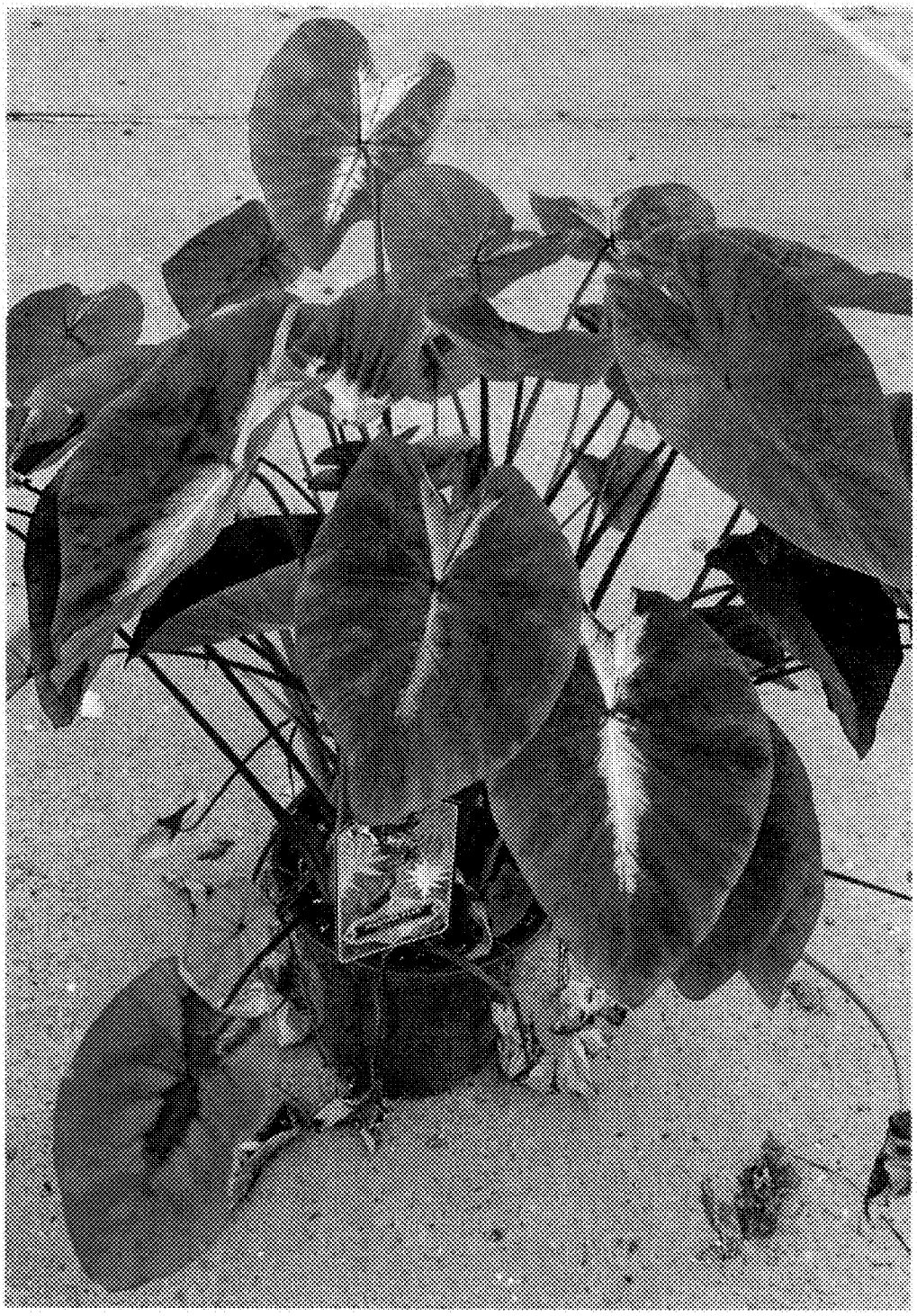
FIG. 3 illustrates, as nearly true as it is reasonably possible to make the same in color photographs of this type, an exemplary 'COMASTA' plant in a marketable state, approximately 8 months old in an 11 cm pot grown in a climate-controlled commercial greenhouse in Louisville, Kentucky, United States.

The following observations and measurements made in January of 2025 describe the approximations of 'COMASTA' plants grown outside in full sun exposure at a nursery in Louisville, Kentucky, United States; as well as a 'COMASTA' plant grown in an 11 cm nursery container at a greenhouse in the same location. While the plants grown outside were exposed to all climate conditions experienced in Louisville, Kentucky, the plant produced in a climate-controlled commercial greenhouse was exposed to 35 percent shade covering and maintained with regular overhead irrigation, slow-release granular fertilizer with a complete analysis, curative chemical pest control measures to control aphids and spider mites, and preventative fungicide applications. These plants observed at different life cycle stages and different exposure to environmental stressors illustrate unique potential changes in the phenotypic qualities of 'COMASTA' plants.

This unique plant exhibits variations in its appearance that may be appreciated as the plant goes through its developmental stages. 'COMASTA' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, Second Edition.

A botanical description of 'COMASTA' and a comparison with the parent plants and most similar commercial comparator are provided below.

Plant description:

*Growth habit*.—Clumping herbaceous perennial with a broad, upright growth habit; Acaulescent, leaves growing from a basal clump.

*General plant profile*.—Broad obovate.

*Height from soil level to top of foliar plane*.—Approximately 185.0 cm.

*Plant spread*.—Approximately 81.28 cm.

*Propagation type*.—Meristematic tissue culture.

*Time to produce a rooted cutting*.—On average 4 weeks to produce a rooted cutting at approximately 29 degrees Celsius.

*Time to produce a finished plant*.—On average 5 weeks to produce a marketable finished plant in an 11 cm pot.

*Disease and pest resistance or susceptibility*.—Neither susceptibility nor resistance to pests and diseases common to *Colocasia* have been observed.

*Environmental tolerances*.—Adapt to temperatures as low as 2 degrees Celsius and as high as 43 degrees Celsius; moderate to high tolerance to rain; low tolerance to wind.

Roots:

*General*.—*Colocasia* sp. exhibit a shallow root system with freely branching fleshy, roots arising from corms which themselves bear detachable cormels. Distribution in the soil profile — Shallow to moderately deep. Texture — Smooth; no root hairs. Color — Greyed-yellow, RHS 161A.

Corms.—Shape — Fusiform. Dimension — 20.5 cm long and 14.0 cm in diameter. Texture — Smooth; glabrous. Color — A combination of brown and greyed-brown, RHS 199A, 199B, and 200D. Cormel — Adherence — Detachable. Shape — Globular. Texture — Densely fibrous. Color — A combination of brown and greyed-brown, RHS 199A, 199B, and 200D.

Foliage:

*Quantity of leaves per shoot*.—On average, 6.

*Arrangement*.—Basal foliage is alternate to spiraled.

*Attachment*.—Petiolate.

*Division*.—Simple.

*Lamina*.—Attitude — Ranging from near horizontal to slightly pendulous. Shape — Broad cordate. Length — 25.4 cm. Width — 15.24 cm. Apex — Acuminate. Base — Cordate; lobes free. Aspect — Concave with strong inversion towards the center of the lamina. Attitude — The lamina is at a 90-degree angle from the petiole at the point of attachment; hanging pendulously. Margins — Entire; heavily undulated. Texture and luster, adaxial surface — Strongly rugose, glabrous, glossy, and strongly to moderately glaucous. Texture and luster, abaxial surface — Strongly rugose, glabrous, glossy, and strongly to moderately glaucous. Color — Juvenile foliage of a plant grown outdoors, adaxial surface — A large, star-shaped central blotch radiates out from the point of attachment to the petiole, following the main vein and lateral veins and extending approximately halfway to the apex of the lamina and three-fourths of the distance to the margins. The central blotch is colored with a marbled blend of yellow-green at and near the point of attachment, RHS 145B and 150B, while the majority of the blotch is colored yellow-white, nearest to RHS 158C, and marginally suffused with red-purple, nearest to a blend of RHS 63D and RHS 70D. The balance of the lamina is colored closest to RHS 135B, and margined with a combination of green and yellow-green; RHS 143C, RHS 144C, and RHS 150B. Juvenile foliage of a plant grown outdoors, abaxial surface — Green closest to RHS 143B. Transitioning foliage of a plant grown outdoors, adaxial surface — Green, nearest to a blend of RHS 131A and 136A, and fading to a lighter shade of green towards the margins, nearest to a combination of RHS 137B and 139C; edged purple, RHS 79C. A large, star-shaped central blotch radiates out from the point of attachment to the petiole, following the main vein and lateral veins and extending approximately halfway to the apex of the lamina and three-fourths of the distance to the margins. The central blotch is colored yellow-white, RHS 158C, and becomes progressively suffused with red-purple as the foliage matures, nearest to a blend of RHS 69B and RHS 70C; the central blotch is irregularly margined with purple, nearest to a blend of RHS 70D, RHS 77A, RHS 78A, and RHS 78B. Transitioning foliage of a plant grown outdoors, abaxial surface — Green, closest to a combination of RHS 141A, RHS 141C, and RHS 141C. Mature foliage of a plant grown outdoors, adaxial surface — Once the plant grown outdoors reaches maturity, the star-shaped central blotch darkens entirely to red-purple, closest to a blend of RHS 64B and 66A, with suffusions of RHS 71A, and occasionally darkening completely to a blend of purple, RHS 77A and 79A; the blotch is margined with purple, RHS 79A. The balance of the lamina is colored violet to dark green, closest to a blend of RHS 83A and RHS 136A. Mature foliage of a plant grown outdoors, abaxial surface — The star-shaped central blotch is red-purple, closest to a blend of RHS 64B and RHS 66A, with suffusions of RHS 71A. The balance of the lamina is colored violet to dark green, closest to a blend of RHS 83A and RHS 136A. Juvenile foliage of a plant grown inside a climate controlled commercial greenhouse, adaxial surface — Green, nearest to a blend of RHS 135B and 136A, and becoming lighter near the margins, nearest to a combination of RHS 143C, 145B, and 150B. A yellow-white central blotch, RHS 158C, broadly borders the main vein and proximal portions of the lateral veins; this blotch becomes progressively suffused with red-purple, a blend of RHS 63D and 70D, as foliage ages. These blotches are irregularly margined with red-purple, nearest to RHS 63D. Juvenile foliage of a plant grown inside a climate controlled commercial greenhouse, abaxial surface — Green, nearest to a blend of RHS 141C and 143A, and transitioning to yellow-green near the margins, nearest to a combination of RHS 143C, 145B, and 150B. A yellow-white central blotch, a blend of RHS 158B and 158C, broadly borders the main vein and proximal portions of the lateral veins. Mature foliage of a plant grown inside a climate controlled commercial greenhouse, adaxial surface — Green, nearest to a combination of RHS 139A, 141A, and 141B, and transitioning to yellow-green near the margins, nearest to a combination of RHS 143C, 145B, and 150B. A red-purple central blotch, a blend of RHS 58A, RHS 61B, RHS 71A, and RHS 72B, broadly borders the main vein and proximal portions of the lateral veins. These blotches are irregularly margined with red-purple, nearest to in between RHS 71A and 72B. Mature foliage of a plant grown inside a climate controlled commercial greenhouse, abaxial surface — Green, nearest to a combination of RHS 139A, 141A, and 141B. A large central blotch broadly borders the main vein and proximal portions of the lateral veins. This central blotch is colored purple, RHS 79C, and suffused with red-purple, distally, nearest to a blend of RHS 71B and 71C; margined with red-purple, RHS 71B.

*Venation*.—Pattern — Pinnate. Color — Adaxial surface of a plant grown outdoors in a juvenile state — Yellow-green, closest to a blend of RHS 145B and RHS 150B surrounding the point of attachment and feathering out towards the base of the lamina. Along the star-like variegation, the midrib and lateral venation are yellow-white, nearest to RHS 158C, gradually transitioning into green distally from the point of attachment, closest to RHS 135B; ultimately transforming to yellow-green where the venation is branching out nearest to the margins, closest to a combination of RHS 135B, RHS 143C, and RHS 144C. Abaxial surface of a plant grown outdoors in a juvenile state — Green, nearest to RHS 135B. Adaxial surfaces of a plant grown outdoors in a transitioning life stage — Yellow-green, closest to a blend of RHS 145B and RHS 150B surrounding the point of attachment and feathering out towards the base of the lamina. Away from the base of the lamina and the point of attachment is yellow-white, nearest to RHS 158C; ultimately becoming a mixture of green and purple, nearest to RHS 131A, RHS 136A, and RHS 79C. Abaxial surface of a plant grown outdoors in a transitioning life stage — Red-purple, closest to a blend of RHS 66A and RHS 74B. Adaxial surfaces of a plant grown outdoors in the mature life stage — Violet, nearest to RHS 83A. Abaxial surfaces of a plant grown outdoors in a mature life stage — Violet, nearest to RHS 83A. Adaxial surfaces of a plant grown in a climate controlled commercial greenhouse — Green, closest to a blend of RHS 135B and 136A. Abaxial surfaces of a plant grown in a climate controlled commercial greenhouse — Purple at the point of attachment and surrounding area proximally to the midrib, nearest to RHS 79C, transitioning to green, nearest to a combination of RHS 139A, RHS 141A, and RHS 141B.

*Petiole*.—Attitude — Outward pendulous. Aspect — Terete. Strength — Very strong. Length — 55.88 cm. Width — 1.27 cm Texture and luster — Smooth, glabrous and glaucous. Petiole color of a plant grown outdoors in the juvenile and intermediary life stages — Purple proximally to the point of attachment, nearest to RHS 79C, transitioning to yellow-green distally from the point of attachment and towards the base of the foliage, nearest to a combination of RHS 147C and RHS 148B. Petiole color of a plant grown outdoors in the mature life stage — Once the plant reaches maturity the petiole darkens completely to purple, nearest to RHS 79C. Petiole color of a plant grown in a climate controlled commercial greenhouse — Purple proximally to the point of attachment, nearest to RHS 79C, transitioning to yellow-green distally from the point of attachment and towards the base of the foliage, nearest to a combination of RHS 147C and RHS 148B. Petiole wings — General description — Two petiole wings extend to about one-third of the length of the petiole, wings attached. Length — 5.08 cm. Width — 0.635 cm. Margin — Entire; not undulated. Texture and luster — Smooth, glabrous, glaucous and glossy. Color — Yellow-green, nearest to a combination of RHS 147C and RHS 148B, narrowly margined with purple, nearest to RHS 79C. This coloration darkens into purple, closest to RHS 79C once the plant reaches maturity.

Inflorescence: *Colocasia* typically produces a spathe and spadix inflorescence, but no flowering has been observed to date.

COMPARISONS WITH THE PARENT PLANTS

Plants of the new cultivar 'COMASTA' differ from the seed parent, 'ColMad1', in the characteristics described in Table 1 below.

TABLE 1

| Characteristic | 'COMASTA' | 'ColMad1' |
|---|---|---|
| General coloration of the petioles. | Yellow-green with petiole wings that are narrowly margined purple, ultimately transitioning entirely to purple. | Red to red-purple. |
| General coloration of the adaxial surface of the mature lamina when grown outdoors. | Violet to dark green and centered with a vivid red-purple coloration in a star-like pattern. | Generally appearing as a homogenous near-black coloration. |
| Foliage texture and luster. | Smooth, glabrous, glaucous and glossy. | Glossy and smooth. |

Plants of the new cultivar 'COMASTA' differ from the parent, 'ColMad2', in the characteristics described in Table 2 below.

TABLE 2

| Characteristic | 'COMASTA' | 'ColMad2' |
|---|---|---|
| General coloration of the petioles. | Yellow-green with petiole wings that are narrowly margined purple, ultimately transitioning entirely to purple. | Green. |
| General coloration of the adaxial surface of the mature lamina when grown outdoors. | Violet to dark green and centered with a vivid red-purple coloration in a star-like pattern. | Generally appearing as homogenously dark green. |

COMPARISONS WITH THE CLOSEST KNOWN COMPARATOR

Plants of the new cultivar 'COMASTA' differ from the closest known commercial comparator, *Colocasia escuelenta* 'FLOCOCLEO' (U.S. Plant Pat. No. 36,569), in the following characteristics described in Table 3 below.

TABLE 3

| Characteristic | 'COMASTA' | 'FLOCOCLEO' |
|---|---|---|
| General coloration of the adaxial surface of the mature lamina when grown outdoors. | Violet to dark green and centered with a vivid red-purple coloration in a star-like pattern. | A blend of darker yellow-greens with a central zone that is colored greyed-purple, generally appearing as dark pink. |
| General coloration of the petioles. | Yellow-green with petiole wings that are narrowly margined purple, ultimately transitioning entirely to purple. | Greyed-purple to purple petioles. |
| Foliage texture and luster. | Rugose, glabrous, glaucous, and glossy. | Smooth, glaucous and glossy. |
| Plant Spread. | 81.28 cm. | 125.0 cm. |

That which is claimed is:

1. A new and distinct variety of *Colocasia* plant named 'COMASTA', substantially as described and illustrated herein.

* * * * *